US012778621B2

(12) United States Patent
Lualdi et al.

(10) Patent No.: US 12,778,621 B2
(45) Date of Patent: Nov. 3, 2026

(54) MILLING DEVICE FOR SURGERY

(71) Applicant: HPF S.R.L., Fagagna (IT)

(72) Inventors: Gabriele Lualdi, Fagagna (IT); Pablo Romano de Agostini, Moimacco (IT)

(73) Assignee: HPF S.R.L., Fagagna (IT)

(*) Notice: Subject to any disclaimer, the term of this patent is extended or adjusted under 35 U.S.C. 154(b) by 606 days.

(21) Appl. No.: 17/725,514

(22) Filed: Apr. 20, 2022

(65) Prior Publication Data

US 2022/0330972 A1 Oct. 20, 2022

(30) Foreign Application Priority Data

Apr. 20, 2021 (IT) ........................ 102021000009938

(51) Int. Cl.
*A61B 17/3207* (2006.01)
*A61B 17/16* (2006.01)
*A61B 17/00* (2006.01)

(52) U.S. Cl.
CPC ................ *A61B 17/320758* (2013.01); *A61B 17/1666* (2013.01); *A61B 2017/00473* (2013.01); *A61B 2017/00477* (2013.01)

(58) Field of Classification Search
CPC ........ A61B 17/1666; A61B 17/320758; A61B 2017/00477; A61B 17/1631; A61B 17/162; A61B 17/1659; A61B 17/1617; A61B 17/1602; A61B 17/1622; A61F 2002/30426
See application file for complete search history.

(56) References Cited

U.S. PATENT DOCUMENTS 4,023,572 A * 5/1977 Weigand ............ A61B 17/1666 606/81
4,712,951 A * 12/1987 Brown ................ B23B 51/0018 606/81
5,980,170 A * 11/1999 Salyer ................ A61B 17/1677 408/239 R
6,102,915 A * 8/2000 Bresler ................. A61F 2/4609 606/80
9,078,672 B1 7/2015 Rosse
2003/0216716 A1* 11/2003 Desarzens ............ A61B 17/162 606/1
2017/0303936 A1* 10/2017 Weekes ...................... F16D 1/02
2018/0153560 A1* 6/2018 Chenaux ............ A61B 17/1666
2020/0015829 A1 1/2020 Khalili et al.

FOREIGN PATENT DOCUMENTS

EP 2 915 493 A1 9/2015
EP 3 427 676 A1 1/2019
WO WO-2015/092377 A1 6/2015

OTHER PUBLICATIONS

Search Report for IT 202100009938, dated Nov. 9, 2021.

* cited by examiner

*Primary Examiner* — Katherine H Schwiker
(74) *Attorney, Agent, or Firm* — MARSHALL, GERSTEIN & BORUN LLP

(57) ABSTRACT

A milling device for surgery, in particular prosthetic surgery, comprising a handling body containing a transmission unit terminating in attachment portions and with which there is rotatably associated a cutter, said device comprising hooking means of the releasable type associated with a distal attachment portion of said attachment portions.

8 Claims, 4 Drawing Sheets

MILLING DEVICE FOR SURGERY

FIELD OF THE INVENTION

The present invention concerns a milling device for surgery, in particular prosthetic surgery, which comprises a handpiece and a cutter rotatably associated with it by means of a connection of the releasable type.

BACKGROUND OF THE INVENTION

Milling devices that can be used during prosthetic surgery of the hip are known.

In normal operating practice, these devices are used to create coordinated and mating acetabular seatings suitable for the disposition and implantation of corresponding acetabular cups.

In particular, known milling devices comprise a handling body, or handpiece, provided with a proximal end, with which a drive member of the manual type or of the motorized type is operatively associated, and a distal end, with which a milling tool, or cutter, is operatively associated, usable to create hemispherical acetabular seatings, or in any case with a spherical cap, suitable for the installation of coordinated acetabular cups of the hip prostheses.

The distal end is provided with attachment means of the releasable type, by means of which the cutter is rotatably secured to the handpiece.

Typically, the attachment means must ensure a stable coupling to the cutter during use, but they must also be easily deactivated in order to release the cutter from the handpiece at the end of the milling operation.

Known attachment means, the shape of which also depends on the coupling means present on the cutter, all have the disadvantage that decoupling them from the handpiece for cleaning the components is particularly complex and requires a certain skill on the part of the operator. This increases the disassembly times and consequently the times associated with cleaning and re-equipping the device for subsequent surgical operations.

This disadvantage also derives from the fact that known attachment means consist of a large number of components.

Moreover, often, the activation mechanism already initially puts the attachment means in a closed position, for example by means of a spring, therefore, in order to attach the cutter, the operator must necessarily first take the attachment means into an open position. This makes the operation of assembling the cutter on the handpiece more difficult.

There is therefore a need to perfect a milling device for surgery, in particular prosthetic surgery, which can overcome at least one of the disadvantages of the state of the art.

In particular, one purpose of the present invention is to provide a milling device for surgery, in particular prosthetic surgery, in which the attachment means between the handpiece and the cutter guarantee both an effective coupling of the handpiece and the cutter, and also an easy uncoupling at the end of the milling operation.

Another purpose of the present invention is to provide such a milling device in which the attachment means consist of a limited number of components.

Another purpose of the present invention is to allow the complete execution of the cleaning steps on all the parts that make up the milling device, without forming dead areas that are not adequately cleaned.

The Applicant has devised, tested and embodied the present invention to overcome the shortcomings of the state of the art and to obtain these and other purposes and advantages.

SUMMARY OF THE INVENTION

The present invention is set forth and characterized in the independent claim. The dependent claims describe other characteristics of the present invention or variants to the main inventive idea.

In accordance with the above purposes, a milling device, in particular for prosthetic surgery, which overcomes the limits of the state of the art and eliminates the defects present therein, comprises a handling body containing a transmission unit terminating in respective attachment portions which comprise a distal attachment portion with which there are associated hooking means of the releasable type for a cutter of the device.

According to one aspect, the hooking means comprise a central body and an annular body mobile with respect to the central body both axially and also angularly with respect to a milling axis, thus selectively defining a condition of releasable clamping and of disengagement of the cutter with respect to the central body.

According to another aspect, the central body comprises a connection portion on which there are hooking slots configured to determine a releasable connection of the bayonet type between a joining portion of the cutter and corresponding apertures parallel to the milling axis.

According to another aspect, the annular body is provided with clamping elements which project in an axial direction toward the connection portion as above, and are configured to be inserted inside the apertures in order to close access to the respective hooking slots when the annular body is in the releasable clamping condition.

According to another aspect, the annular body comprises magnetic elements configured to allow the releasable coupling to the connection portion as above.

According to another aspect, the annular body is axially constrained to move in abutment between the handling body and the connection portion.

According to another aspect, in the releasable clamping condition the cutter is integral with the central body.

According to another aspect, with a proximal attachment portion of the attachment portions, which comprises a base, a coupling head and a plate located intermediate, there is associated a connection adapter provided with a joining cavity having a shape mating with that of the coupling head and of the plate, in such a way as to contain them completely.

According to another aspect, the connection adapter as above has a circular lip which envelops the plate circumferentially.

BRIEF DESCRIPTION OF THE DRAWINGS

These and other aspects, characteristics and advantages of the present invention will become apparent from the following description of some embodiments, given as a non-restrictive example with reference to the attached drawings wherein.

Figure 1:
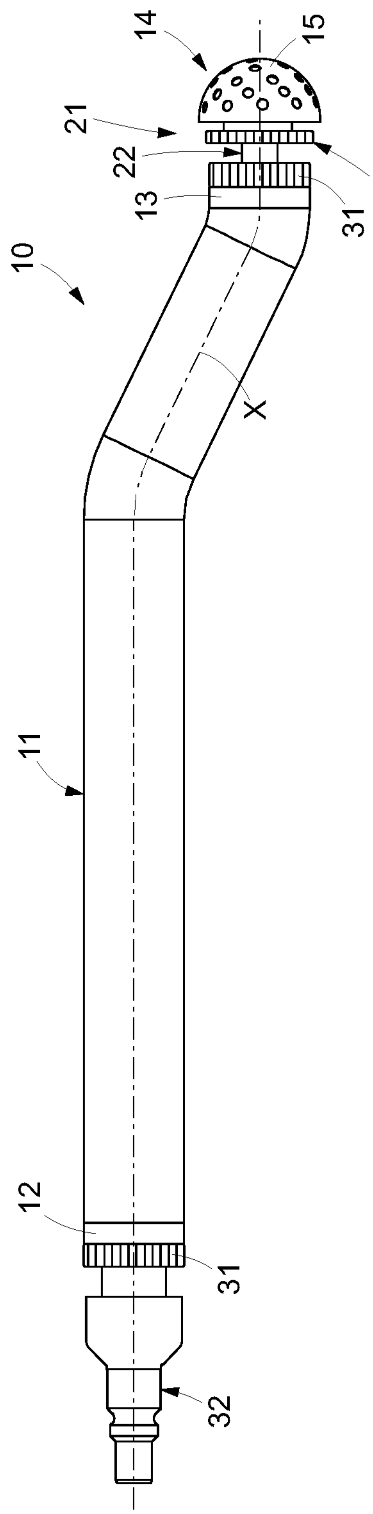
FIG. 1 is a lateral view of a milling device for prosthetic surgery in accordance with some embodiments described here.

To facilitate comprehension, the same reference numbers have been used, where possible, to identify identical common elements in the drawings. It is understood that elements and characteristics of one embodiment can be conveniently combined or incorporated into other embodiments without further clarifications.

DESCRIPTION OF SOME EMBODIMENTS

We will now refer in detail to the possible embodiments of the invention, of which one or more examples are shown in the attached drawings, by way of a non-limiting illustration. The phraseology and terminology used here is also for the purposes of providing non-limiting examples.

With reference to FIG. 1, a milling device 10 for surgery is shown, more specifically for hip joint prosthetic surgery operations.

The device 10 comprises a handling body 11 which has an oblong shape and develops along a milling axis X between a proximal end 12 and a distal end 13 opposite each other.

With particular reference to FIGS. 3-4 and FIGS. 7-8, the device 10 also comprises a cutter 14 having a milling cap 15 and a joining portion 16 stably fixed to the base of the milling cap 15 and provided with radial arms 17 for connection with the handling body 11. The radial arms 17 can have the shape of spokes 17', FIGS. 3-4, or they can be tubular elements 17" transverse to each other disposed so as to form a cross, FIGS. 7-8.

Figure 2A:
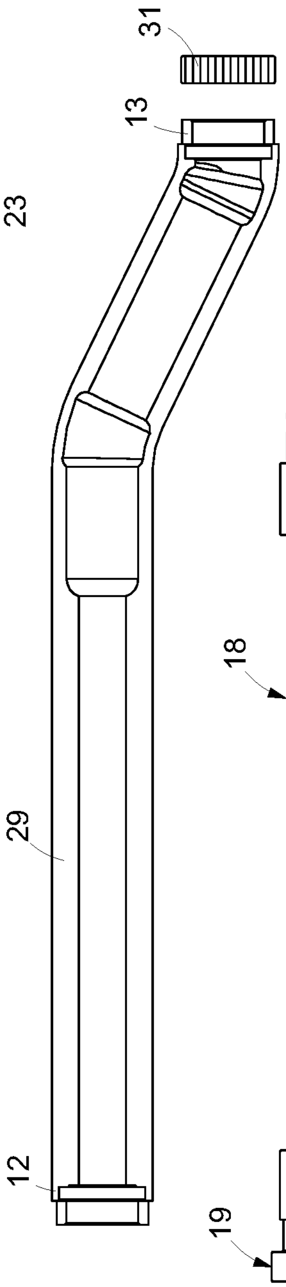
FIGS. 2*a*-2*c* show exploded views of FIG. 1, in particular of the handpiece (FIG. 2*a* and FIG. 2*c*) and of the movement unit (FIG. 2*b*)
Figure 2B:
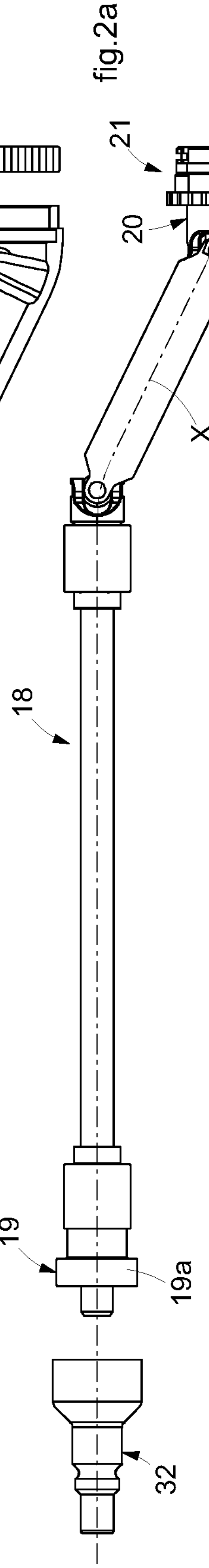
Figure 2C:
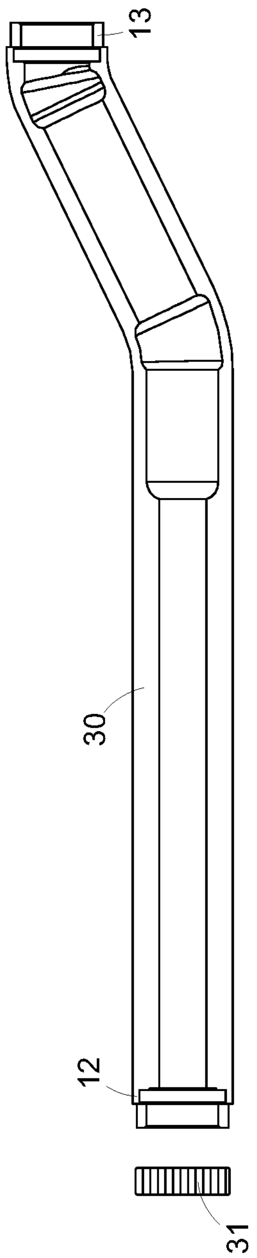

With particular reference to FIGS. **2*a*-2*c*, the device 10 comprises a rotary motion transmission unit 18, FIG. 2*b*, disposed inside the handling body 11, which develops from the proximal end 12 to the distal end 13, FIG. 2*a* and FIG. 2*c***.

The transmission unit 18 ends in respective attachment portions 19, 20 which exit from the handling body 11.

The attachment portions 19, 20 comprise a proximal attachment portion **19*a* and a distal attachment portion 20*a* which are respectively configured to connect in a releasable manner to a drive member, of the manual or motorized type, and to the cutter 14**.

The transmission unit 18 therefore allows to transmit the rotary motion, generated by the drive member, from the proximal attachment portion **19*a* to the distal attachment portion 20*a***.

The device 10 comprises hooking means 21 of the releasable type associated with the distal attachment portion **20*a*, visible for example in FIG. 2*b***.

The hooking means 21 have a central body 22 and an annular body 23, mobile with respect to the central body 22 both axially and also angularly with respect to the milling axis X, thus selectively defining a condition of releasable clamping and a condition of disengagement of the cutter 14 (FIG. 3, FIG. 5 and FIG. 7, FIG. 9) with respect to the central body 22.

In the releasable clamping condition, the cutter 14 is integral with the central body 22 which is fixed to the distal attachment portion **20*a* which is able, during use, to determine its rotation and therefore to impart, as a consequence, the rotation of the cutter 14**.

The central body 22 comprises a connection portion 24 on which there are hooking slots 25, configured to determine a releasable bayonet-type connection between the joining portion 16 of the cutter 14 and the central body 22.

The connection portion 24 develops circumferentially.

Figure 3:
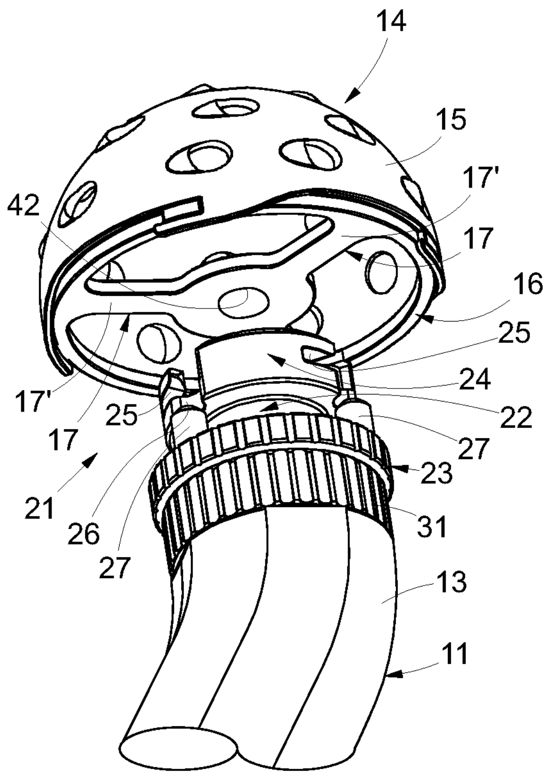
FIGS. 3-4 are three-dimensional views showing the connection between one embodiment of the cutter and the handpiece by means of the releasable hooking means.
Figure 4:
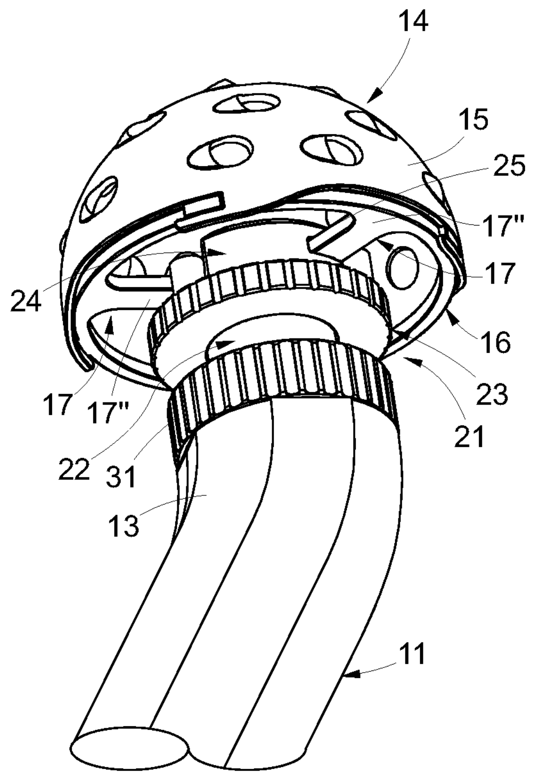
Figure 5:
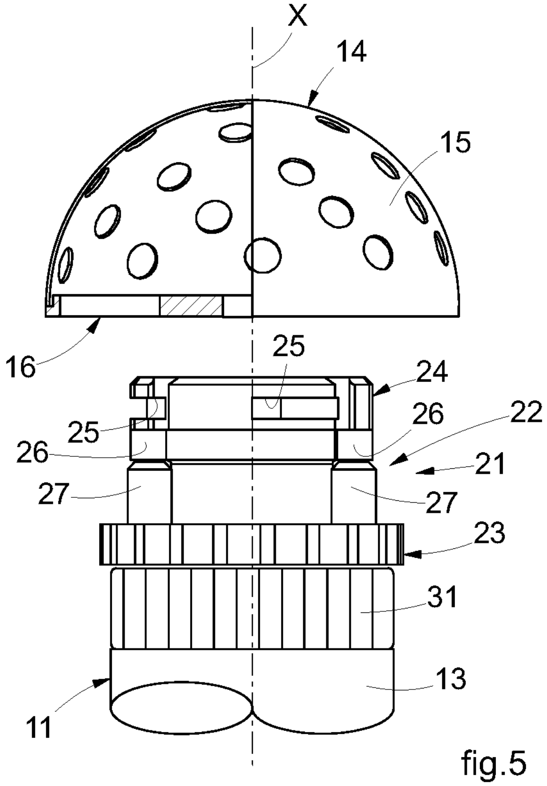
FIGS. 5-6 are partial section views along a plane passing through the milling axis respectively of FIGS. 3-4.
Figure 6:
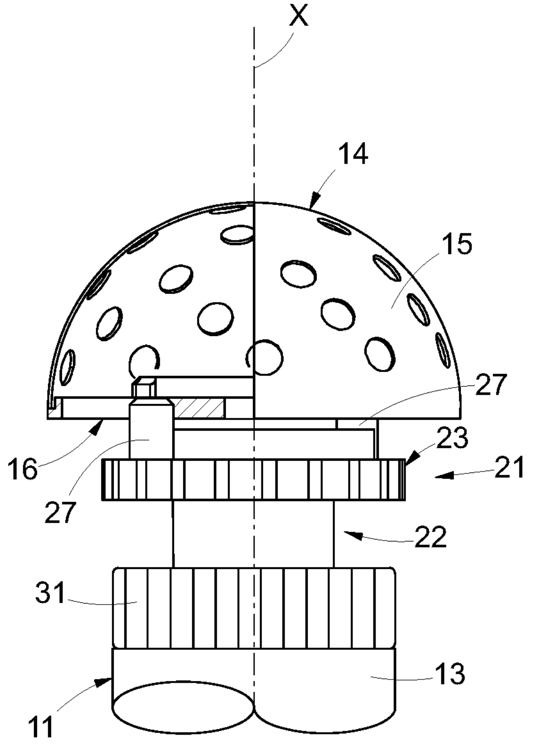
Figure 7:
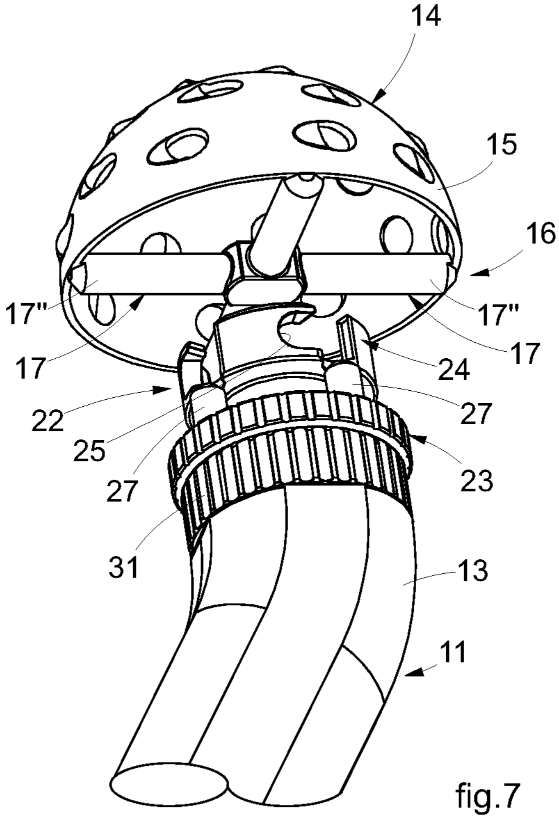
FIGS. 7-8 are three-dimensional views showing the connection between another embodiment of the cutter and the handpiece.
Figure 8:
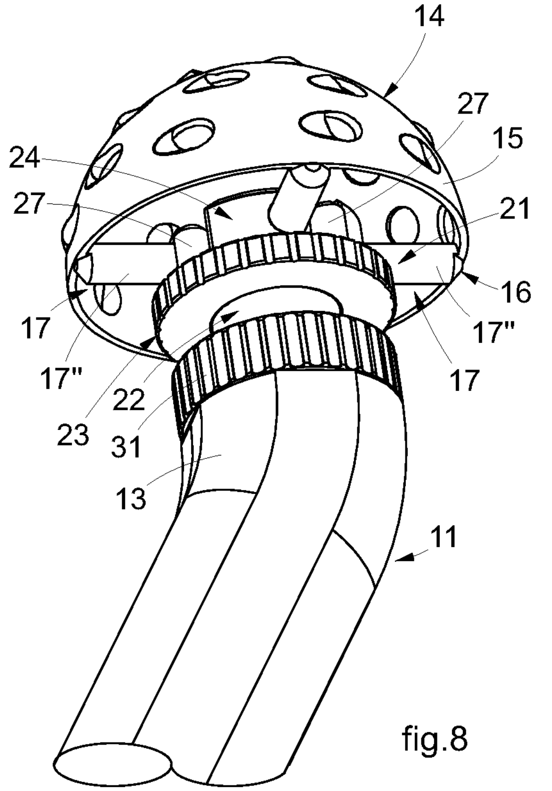
Figure 9:
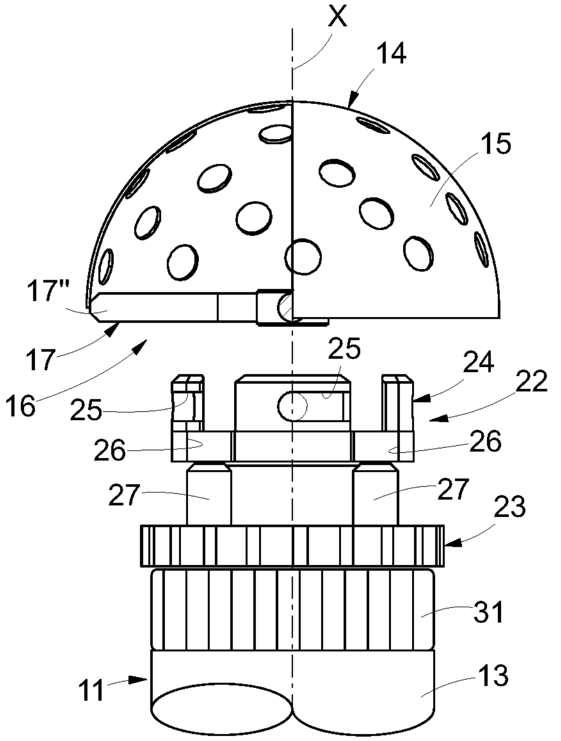
FIGS. 9-10 are partial section views along a plane passing through the milling axis respectively of FIGS. 7-8.
Figure 10:
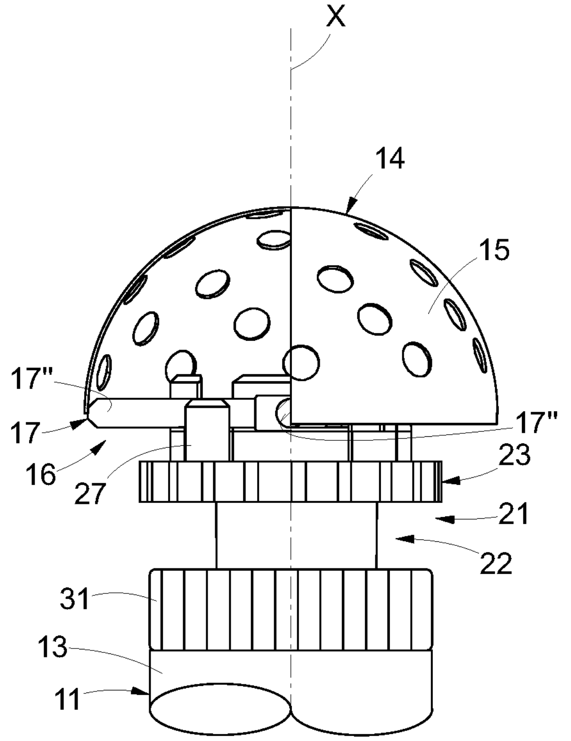
Figure 11:
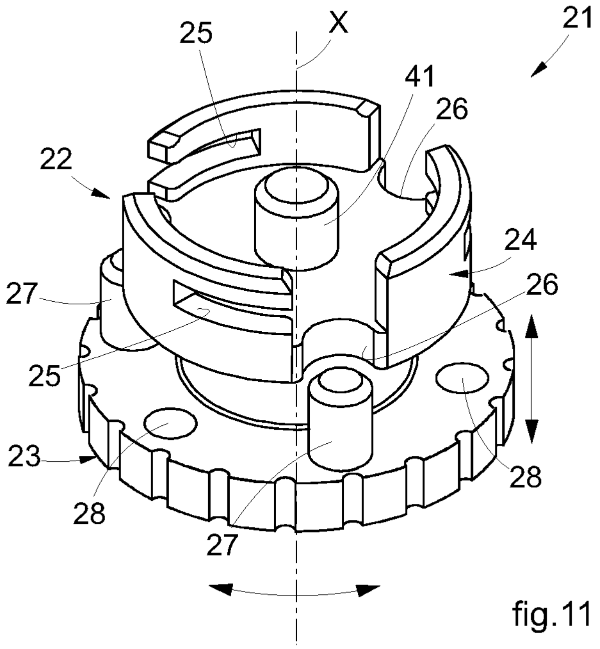
FIGS. 11-12 show respective three-dimensional views of the hooking means in which the annular body is in a condition of disengagement.

The central body 22 can comprise, as in the example of FIG. 11, a central pin 41 configured to be inserted into a mating central aperture 42, visible in FIG. 3, of the joining portion 16 of the cutter 14 in order to increase the stability of the connection.

With reference to FIG. 5, FIG. 9 and FIGS. 11-12, the connection portion 24 has, in correspondence with each hooking slot 25, an aperture 26 configured to receive a clamping element able to close access to the hooking slot 25 when the annular body 23 is in the releasable clamping condition and the joining portion 16 of the cutter 14 is engaged.

The hooking slots 25 develop in a direction substantially orthogonal to the milling axis X, while the access through which the joining portion 16 of the cutter 14 is inserted/extracted develops in an axial direction and is aligned with a respective one of the apertures 26.

The apertures 26 are parallel to the milling axis X.

The apertures 26 can be made as recesses, holes, slots or in another known way. In the example described here, the apertures 26 are open radially toward the outside of the central body 22, more in particular toward the outside of the connection portion 24, FIGS. 11-12.

The annular body 23 is provided with clamping elements, or pegs, 27 which project in an axial direction toward the connection portion 24 of the central body 22 and are configured to be inserted inside the apertures 26 in order to close access to the respective hooking slots 25 when the annular body 23 is in the releasable clamping condition as above. The annular body 23, since it is rotatable around the milling axis X, that is, around the central body 22, can be moved in rotation so as to make the pegs 27 coincide with the apertures 26 for their axial insertion.

The presence of the pegs 27 that clamp the cutter 14 in position guarantees high stability even in the event of a slowing down of the rotation of the cutter 14, or if the cutter 14 is used both in one sense and the other, for example during particular phases of the surgical operation.

According to some embodiments, the shape of the hooking slots 25 is mating with the shape of the radial arms 17 of the joining portion 16 of the cutter 14. In the example embodiment of FIGS. 3-6 and FIG. 11, the hooking slots 25 have an elongated profile mating with the shape/thickness of the spokes 17', while in the example embodiment of FIGS. 7-10 and FIG. 12 the hooking slots 25 have a profile shaped as an arc of a circle, mating with the profile of the tubular elements 17" which are substantially cylindrical. The axial section of the radial arms 17 can in any case be of any shape whatsoever.

Figure 12:
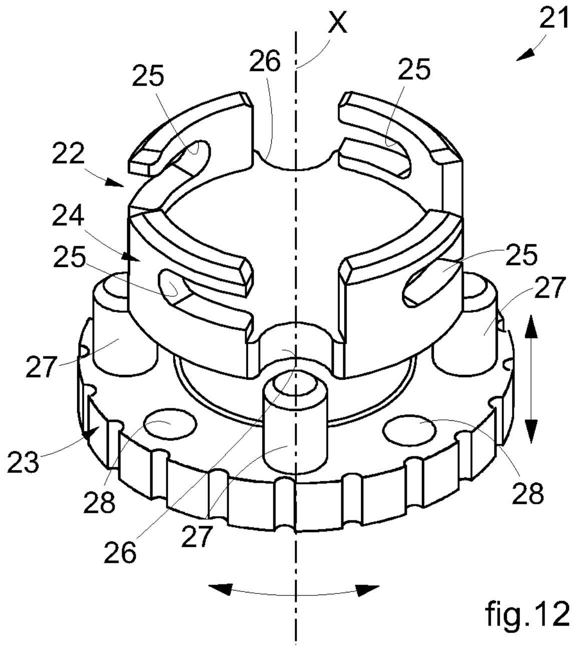
Figure 13:
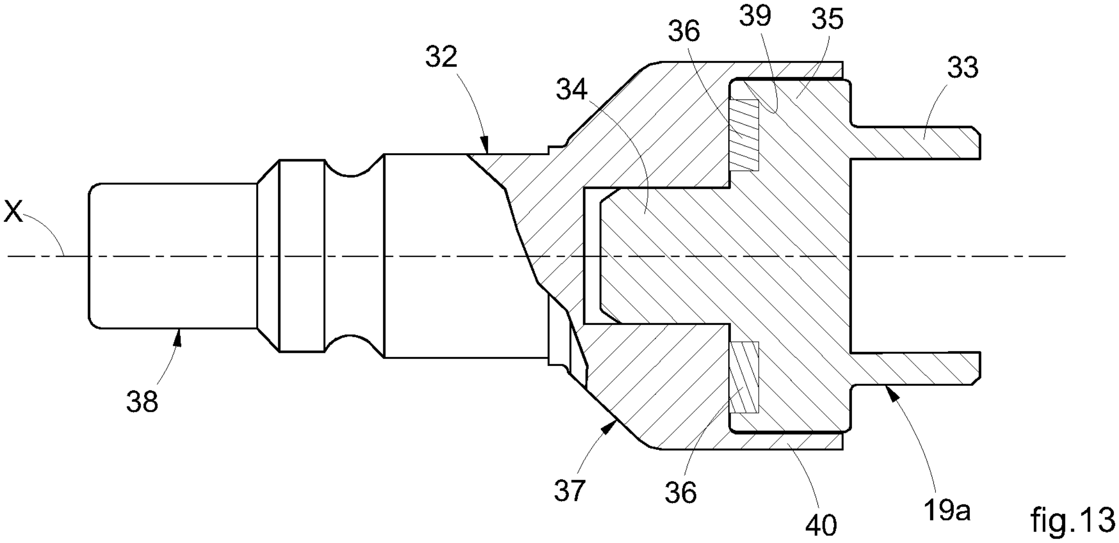
FIG. 13 shows a partial section view of the proximal attachment portion with which there is associated a connection adapter for the hooking to a motorized drive member.

The annular body 23 comprises magnetic elements, or magnets, 28 configured to allow the releasable coupling to the connection portion 24 of the central body 19, FIGS. 11-12.

The annular body 23 is axially constrained to move in abutment between the handling body 11 and the connection portion 24 of the central body 19. The connection portion 24 has an overall radial size larger than that of the aperture of the annular body 20, in such a way as to create an abutment for the latter.

In particular, the annular body 23 is free to move in abutment between the handling body 11 and the connection portion 24, without constraints imposed by elastic elements or other mechanisms.

The hooking slots 25 have a circumferential depth such as to completely contain the part of the joining portion 16 which, during use, is inserted therein.

When the joining portion 16 is engaged in the hooking slots 25 and the annular body 23 is coupled to the connection portion 24 in the releasable clamping condition, the pegs 27 clamp the cutter 14 in the desired angular position and make it integral with the central body 22, through which it is made to rotate, FIGS. 4, 6 and FIGS. 8, 10.

The clamping of the annular body 23 to the connection portion 24 is guaranteed by the magnetic elements 28, which simplify the uncoupling of the annular body 23 for the extraction of the cutter 14.

According to possible embodiments, the central body 22 is fixed in an unmovable manner to the proximal attachment portion 19*a* of the transmission unit 18. In this way, the cleaning of the components occurs without needing to separate the various pieces.

The transmission unit 18 is almost entirely contained within the handling body 11, which consists of a first shell 29, FIG. 2*a*, and a mating second shell 30, FIG. 2*c*, which can be stably coupled to each other in a releasable manner.

The first and second shells 29, 30 are identical and specular, coupled to each other by means of tightening nuts 31 coaxial to the milling axis X and present on both the proximal 12 and also the distal 13 ends.

According to some embodiments, with the proximal attachment portion 19*a* there can be associated a connection adapter 32 for the hooking to a motorized drive member, FIGS. 1-2*b* and FIG. 13.

In particular, the proximal attachment portion 19*a* comprises a base 33, a coupling head 34 and a plate 35 located intermediate, wherein the plate 35 is provided with magnetic elements 36.

The connection adapter 32 comprises a universal attachment part 37, able to be hooked to the proximal attachment portion 19*a*, and a specialized attachment part 38, able to be hooked to the specific motorized drive member.

The universal attachment part 37 is provided with a joining cavity 39 having a shape mating with that of the coupling head 34 and of the plate 35, in such a way as to contain them completely.

In particular, the connection adapter 32 has, in correspondence with the universal attachment part 37, a circular lip 40 which envelops the plate 35 circumferentially and prevents an undesired "oscillation" effect, making the connection more stable and safer.

It is clear that modifications and/or additions of parts may be made to the milling device for prosthetic surgery as described heretofore, without departing from the field and scope of the present invention as defined by the claims.

In the following claims, the sole purpose of the references in brackets is to facilitate reading: they must not be considered as restrictive factors with regard to the field of protection claimed in the specific claims.

The invention claimed is:

1. A milling device for surgery comprising: a handling body containing a transmission unit terminating in attachment portions which comprise a distal attachment portion having releasable hooking means for attaching a cutter of said milling device, wherein said hooking means comprise a central body and an annular body moveable axially with respect to said central body thus selectively defining a releasable clamping condition and a disengagement condition of said cutter with respect to said central body;

wherein said central body comprises a connection portion having hooking slots configured to form a releasable bayonet-type connection between a joining portion of said cutter and corresponding apertures parallel to a milling axis (X);

wherein said annular body is provided with clamping elements which project in an axial direction toward said connection portion, the clamping elements being configured to be inserted inside said corresponding apertures in order to close access to the respective hooking slots when said annular body is in said releasable clamping condition;

wherein the annular body is free to move axially in abutment between the handling body and the connection portion of the central body; and further wherein the annular body comprises magnets sized and arranged to engage the connection portion when the annular body is in abutment with the connection portion thereby forming a releasable magnetic coupling between the annular body and the connection portion.

2. The milling device as in claim 1, wherein in said releasable clamping condition said cutter is integral with said central body.

3. The milling device as in claim 1, wherein the attachment portions include a proximal attachment portion which comprises a base, a coupling head and an intermediate plate, and including a connection adapter provided with a joining cavity having a shape mating with a shape of said coupling head and of said plate in order to contain the coupling head and the plate.

4. The milling device as in claim 3, wherein said connection adapter has a circular lip which envelops said plate circumferentially.

5. The milling device as in claim 1, wherein the central body comprises a central pin configured for insertion into a mating central aperture of the joining portion of the cutter.

6. The milling device as in claim 1, wherein the magnets are further arranged to guarantee the forming of the releasable magnetic coupling and are further arranged to allow uncoupling of said annular body from the connection portion when extracting the cutter.

7. The milling device as in claim 1, wherein said annular body is free to move axially without resistance imposed by elastic spring elements.

8. A milling device for surgery comprising:

a handling body containing a transmission unit terminating in attachment portions which comprise a distal attachment portion having releasable hooking means for attaching a cutter of said milling device, wherein said hooking means comprise a central body and an annular body moveable axially with respect to said central body, the annular body further being rotatable about a milling axis (X) thus selectively defining a releasable clamping condition and a disengagement condition of said cutter with respect to said central body;

wherein said central body comprises a connection portion having hooking slots configured to form a releasable bayonet-type connection between a joining portion of said cutter and corresponding apertures parallel to said milling axis (X), wherein said apertures are oriented to face radially outward relative to the central body;

wherein the annular body is free to move axially in abutment between the handling body and the connection portion of the central body without resistance imposed by elastic spring elements;

wherein said annular body is provided with pegs configured to project in an axial direction toward said connection portion, the pegs being configured to be inserted inside said corresponding apertures in response to movement of the annular body to abutment with the connection portion in order to block the respective hooking slots when said annular body is in said releasable clamping condition;

further wherein said annular body comprises magnets configured to engage the connection portion when the annular body is in abutment with the connection portion to thereby form and maintain a releasable coupling with the connection portion.

* * * * *